(12) United States Patent
Steffensmeier et al.

(10) Patent No.: US 11,234,744 B2
(45) Date of Patent: Feb. 1, 2022

(54) IMPLANT POSITIONING DEVICES AND METHODS

(71) Applicant: Jace Medical, LLC, Winona Lake, IN (US)

(72) Inventors: Scott Steffensmeier, Winona Lake, IN (US); Jason Detweiler, Warsaw, IN (US); Justin James May, Leesburg, IN (US)

(73) Assignee: Jace Medical, LLC, Winona Lake, IN (US)

( * ) Notice: Subject to any disclaimer, the term of this patent is extended or adjusted under 35 U.S.C. 154(b) by 217 days.

(21) Appl. No.: 16/263,100

(22) Filed: Jan. 31, 2019

(65) Prior Publication Data

US 2019/0167320 A1    Jun. 6, 2019

Related U.S. Application Data

(63) Continuation of application No. 14/831,422, filed on Aug. 20, 2015, now Pat. No. 10,226,290.

(60) Provisional application No. 62/039,672, filed on Aug. 20, 2014.

(51) Int. Cl.
*A61B 17/17* (2006.01)
*A61B 17/86* (2006.01)
*A61B 17/90* (2006.01)
*A61B 17/80* (2006.01)

(52) U.S. Cl.
CPC ........ *A61B 17/808* (2013.01); *A61B 17/1728* (2013.01); *A61B 17/1789* (2016.11); *A61B 17/865* (2013.01); *A61B 17/8023* (2013.01); *A61B 17/8076* (2013.01); *A61B 17/90* (2021.08)

(58) Field of Classification Search
CPC .............. A61B 17/808; A61B 17/1789; A61B 17/1728; A61B 17/865
USPC ....................................... 606/86 B
See application file for complete search history.

(56) References Cited

U.S. PATENT DOCUMENTS

| | | | |
|---|---|---|---|
| 2005/0124990 A1* | 6/2005 | Teague | A61F 2/2875 606/53 |
| 2005/0177163 A1* | 8/2005 | Abdou | A61B 17/808 606/252 |
| 2011/0004254 A1* | 1/2011 | Beger | A61B 17/1728 606/289 |

* cited by examiner

*Primary Examiner* — Matthew J Lawson
(74) *Attorney, Agent, or Firm* — Taylor IP, P.C.

(57) ABSTRACT

An implant positioning device including a guide and holder for fasteners used in orthopaedic fixation for use in affixing a plate-like member to a bone or other part of a patient. The guide and holder includes a base adapted to align with the plate in a manner to orient fasteners with the plate for fixation. A plurality of fastener holders are on the base and adapted to releasably hold a fastener in a manner where the fastener is exposed at a proximal end for access by a fastener driver and aligned at a distal end with an aperture on the plate through which the fastener is to be driven.

19 Claims, 17 Drawing Sheets

IMPLANT POSITIONING DEVICES AND METHODS

CROSS REFERENCES TO RELATED APPLICATIONS

This application is a continuation of U.S. patent application Ser. No. 14/831,422 entitled Implant Positioning Devices and Methods, filed Aug. 20, 2015, which claims the benefit of U.S. Provisional Patent Application Ser. No. 62/039,672 entitled Orthopaedic Fixation Device, filed Aug. 20, 2014, the contents of which are incorporated herein by reference in their entirety.

FIELD

The disclosure relates generally to implant positioning apparatuses and devices. More particularly, the disclosure relates to implant positioning apparatuses and devices for use in bone fixation, sternum fixation, and other orthopaedic fixation procedures.

BACKGROUND

In some surgical procedures involving bones, for instance, the procedure may involve separating a bone into portions, which are thereafter reunited. This happens, for example, in entries into the chest cavity, as for heart surgery, where the sternum is required to be separated along its length. There may be other instances where a bone has undergone fracturing through some trauma, and is thereafter to have portions rejoined for proper healing. Additionally, in applications involving the spine, there may be independent bones that benefit from holding a particular position relative to each other to allow for healing of the disc and other surrounding tissues.

The bones or skeletal tissue, or combinations of bone and tissue, can be held secure to one another in adjacency using a fixation device, or system. Many kinds of conventional fixation devices include wires or cables that are organized to pull the bone portions together, laterally across a divide or fracture. However, these types of fixation devices can be relatively complex to emplace. For instance, if a plate-type structure is to be attached to a bone, it is important to locate the fixation points (e.g., for screws) very accurately, as for drilling pilot holes for the screws. Plainly, speed and ease in then attaching the structure are significant considerations.

SUMMARY

Implant positioning devices are disclosed for assisting in positioning orthopaedic fixation devices (such as bone plates, etc.) for use in bone fixation, sternum fixation, and other orthopaedic fixation procedures. In an embodiment, the implant positioning device includes a compression attachment mechanism configured to removably couple to a plate. A fastener guide is coupled to the compression attachment mechanism and configured to receive a fastener, and a spring member is disposed in the fastener guide and configured to hold the fastener in the fastener guide.

In another embodiment, a combined guide and holder for fasteners used in orthopaedic fixation is disclosed, wherein a plate is to be affixed to a bone. In this embodiment, the device includes a base or frame adapted to align with the plate in a manner to orient fasteners with the plate for fixation. Further, a plurality of fastener holders are on the base, with each fastener holder adapted to releasably hold a fastener in a manner where the fastener is exposed at a proximal end for access by a fastener driver and aligned at a distal end with an aperture in the plate through which the fastener is to be driven.

In yet another embodiment, a device for positioning an orthopaedic fixation device has a base, including: a mounting structure, a first fastener guide coupled to the mounting structure, and a second fastener guide coupled to the mounting structure, wherein the mounting structure is between the first and second fastener guides. A compression attachment mechanism is also coupled to the base and configured to releasably hold a plate and align the plate with at least one of the first and second fastener guides.

The implant positioning device may also be used to affix fasteners to a bone or other body part in a designed pattern without a plate or the like being fixed therein.

DETAILED DESCRIPTION

Figure 1:
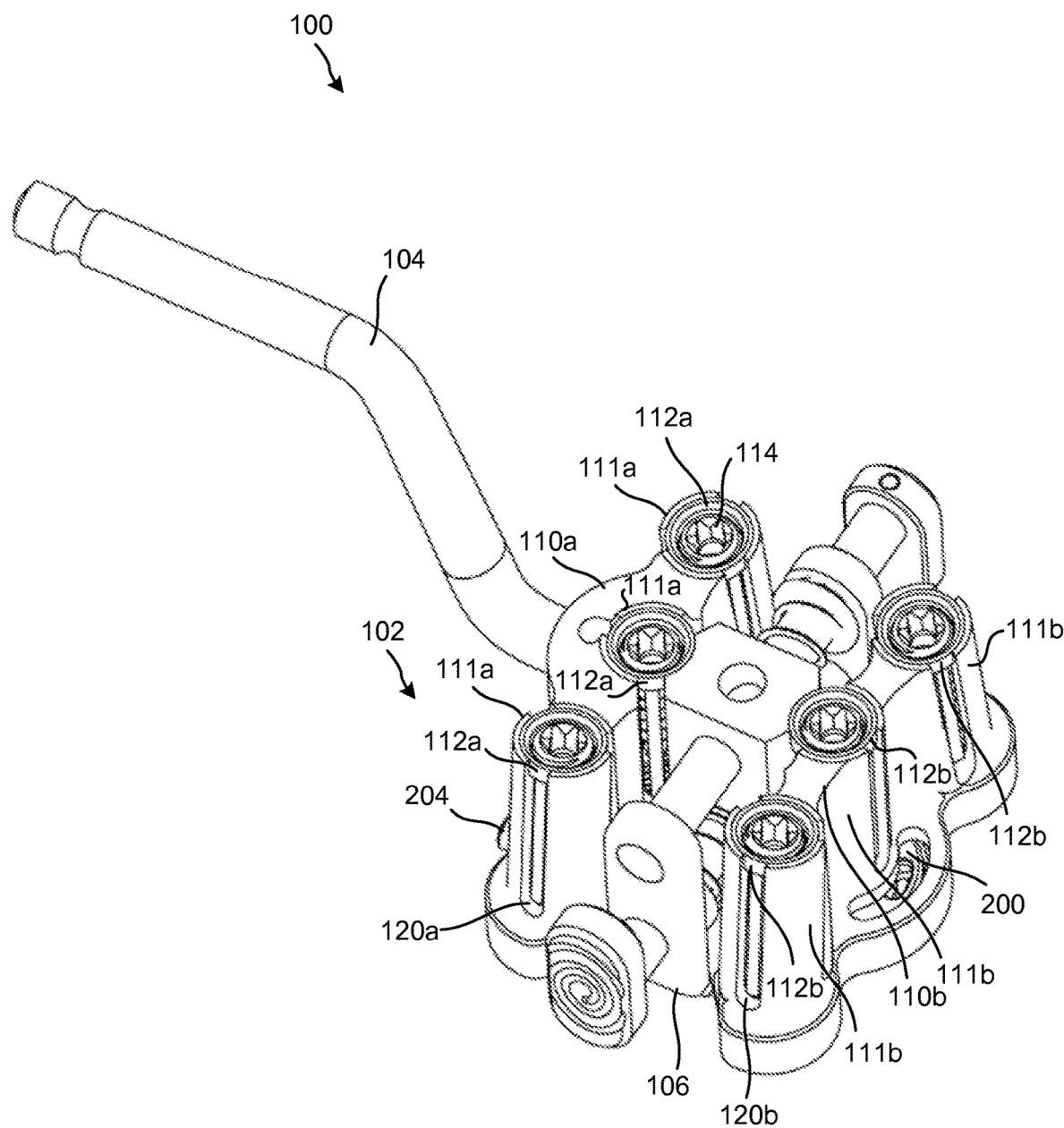
FIG. 1 illustrates a first perspective view of an implant positioning device in accordance with an embodiment of the disclosure.
Figure 2:
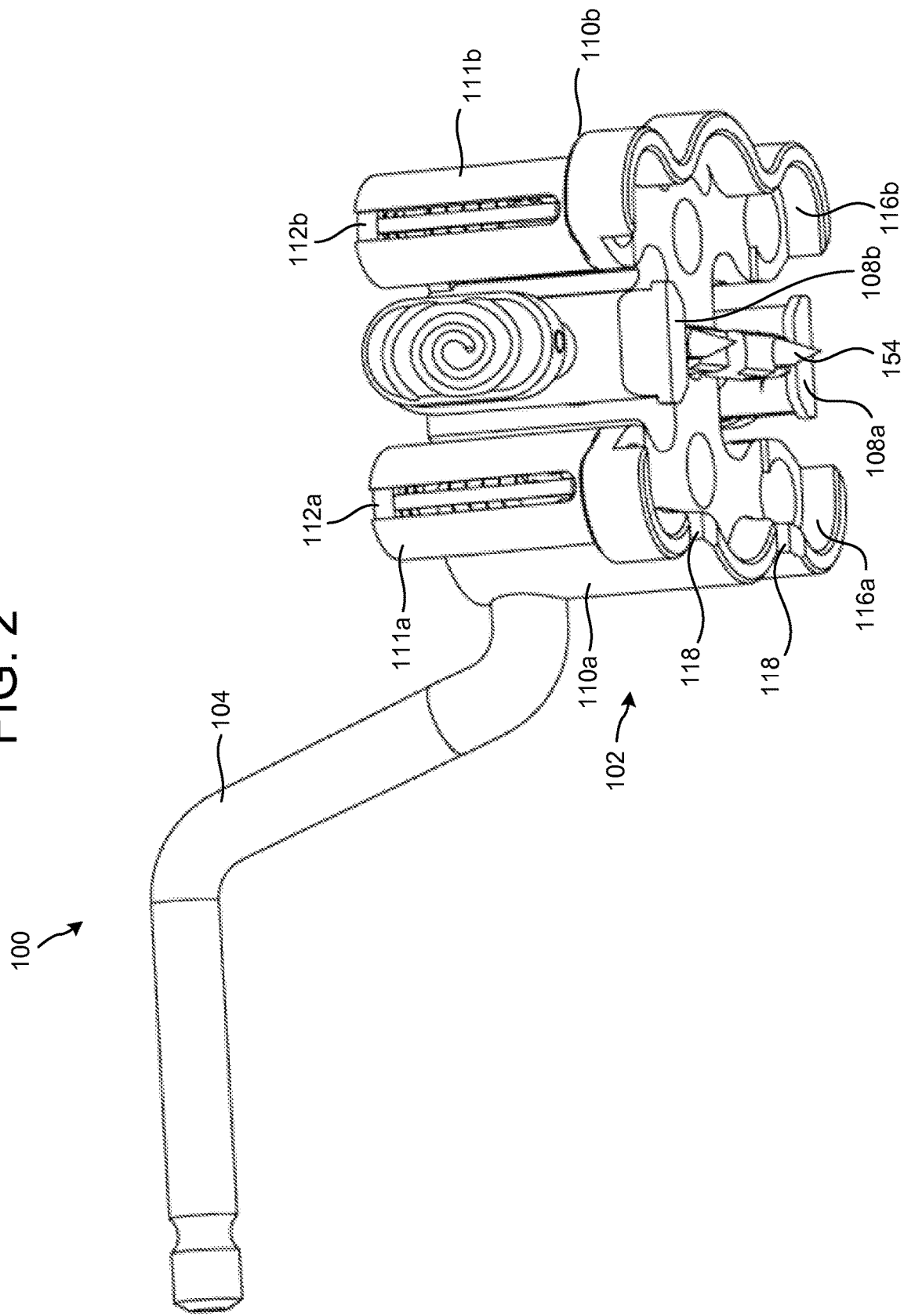
FIG. 2 illustrates a second perspective view of the implant positioning device of FIG. 1 in accordance with an embodiment of the disclosure.

While the embodiments described hereinafter are in the environment of positioning devices, systems and methods for use in positioning orthopaedic fixation devices on the sternum, it should be appreciated that the disclosure has broader application, such as where bone or other calcaneus body parts require fixation features, such as screws, pins, or other fastener, to be located and placed.

FIGS. 1-5 illustrate an implant positioning device 100 in the form of a combined drill guide and fixation element holder according to an embodiment of the disclosure. As illustrated, the implant positioning device 100 includes a frame or body portion 102, a handle portion 104 coupled to the body portion 102, and a compression attachment mechanism 106 including attachment feet 108a and 108b.

The body 102 includes one or more sets of fastener guides (for example, a first set of fastener guides 110a and a second set of fastener guides 110b) on opposite sides of the body 102. The first set of fastener guides 110a includes one or more first fastener holders or fastener housing members 111a capable of holding fastener captive elements 112a respectively disposed in each of the fastener housing members 111a. Similarly, the second set of fastener guides 110b includes one or more second fastener housing members 111b capable of holding fastener captive elements 112b respectively disposed in each of the fastener housing members 111b. The fastener captive elements 112a and 112b may be a spring element, o-ring, etc. The first and second sets of fastener guides 110a and 110b provide fastener housings 111a and 111b to hold, position, and guide fasteners 114 for insertion into and through fastener apertures in one or more plates 200 (which may include a first plate 202a and a second plate 202b illustrated in FIG. 3) to install the plate(s) 200 on a bone, calcaneus body part, or other area of a patient. The plates 200 may be the plates disclosed in U.S. Patent Application Publication No. 2015/0119887, entitled Orthopedic Fixation Device, System and Method, filed Oct. 27, 2014, the disclosure of which is incorporated by reference herein in its entirety.

As illustrated, there are two sets of fastener guides, the first and second sets of fastener guides 110a and 110b, (one disposed on each side of the body 102), with each set respectively including three fastener housings 111a and 111b, and the fasteners 114 are screws. However, there may be more or less than three fastener housings 111a and 111b in each set of fastener guides and the fasteners may be pins, rivets, and other types of fasteners, etc.

In this embodiment, the first and second sets of fastener guides 110a and 110b provide the fastener housings 111a and 111b in the form of substantially cylindrical, hollow, tube like guide barrels that are positioned to align with the fastener apertures in the plate(s) 200. The first and second fastener housings 111a and 111b communicate with respective first and second recesses 116a and 116b in a bottom of the body 102. The respective first and second recesses 116a and 116b are respectively sized and shaped to receive the corresponding first and second plates 202a and 202b. For example, referring to FIGS. 2-4, the first recess 116a is sized and shaped to receive the first plate 202a, and the second recess 116b is sized and shaped to receive the second plate 202b. As illustrated, the first plate 202a includes shear bars or pins 204. In this respect, the first sets of fastener guides 110a includes grooves 118 that communicate with the first recess 116a. The grooves 118 are sized and shaped to receive the corresponding pins 204 when the first plate 202a is received in the first recess 116a and the pins 204 are in an undeployed position (as illustrated in FIG. 4).

When in use, the first and second plates 202a and 202b are respectively disposed in the corresponding first and second recesses 116a and 116b and a bottom portion of the fastener housings 111a and 111b are in close proximity to the plate(s) 202a and 202b to minimize the opportunity for any unintentional angulation of the fasteners 114 as the fasteners 114 pass through the respective guides of the first and second sets of fastener guides 110a and 110b. While the first and second sets of fastener guides 110a and 110b are illustrated as positioned to align with the fastener apertures of the plate(s) 200, the first and second sets of fastener guides 110a and 110b may be positioned to align with apertures of any plate(s) or other device, and/or the location of the guides in each of the first and second sets of fastener guides 110a and 110b may be adapted or modified to align with apertures of any plate(s) or other device. The implant positioning device 100 may also be used to locate and attach fasteners to a bone or other body part without any plate or the like being involved.

The first and second sets of fastener guides 110a and 110b may also be used to guide a driver and/or drill depending on the application. The first and second sets of fastener guides 110a and 110b may also be used to guide other instruments, for example, to place markings, pegs, headless pins, etc. in a bone, which then serve as locating features to place plates or any other device before or after a resection is made.

In an aspect, the first and second sets of fastener guides 110a and 110b may be disposable, and pre-loaded with fasteners. For example, the first and second sets of fastener guides 110a and 110b may be removable from the compression attachment mechanism 106. This allows the first and second sets of fastener guides 110a and 110b to be easily replaced during a surgical procedure.

As illustrated, each of the fastener housings 111a and 111b of the first and second sets of fastener guides 110a and 110b may include one or more side apertures or slits. For example, each of the fastener housings 111a includes first side slits or apertures 120a, and each of the fastener housings 111b includes second side slits or apertures 120b. The first and second side apertures 120a and 120b for one or more finger-like structures that make up the fastener housings 111a and 111b. These finger-like structures allow for ease of cleaning and sterilization of the implant positioning device 100. The first and second side apertures 120a and 120b may also receive and serve as expansion zones for the fastener captive elements 112a and 112b, respectively.

Figure 5:
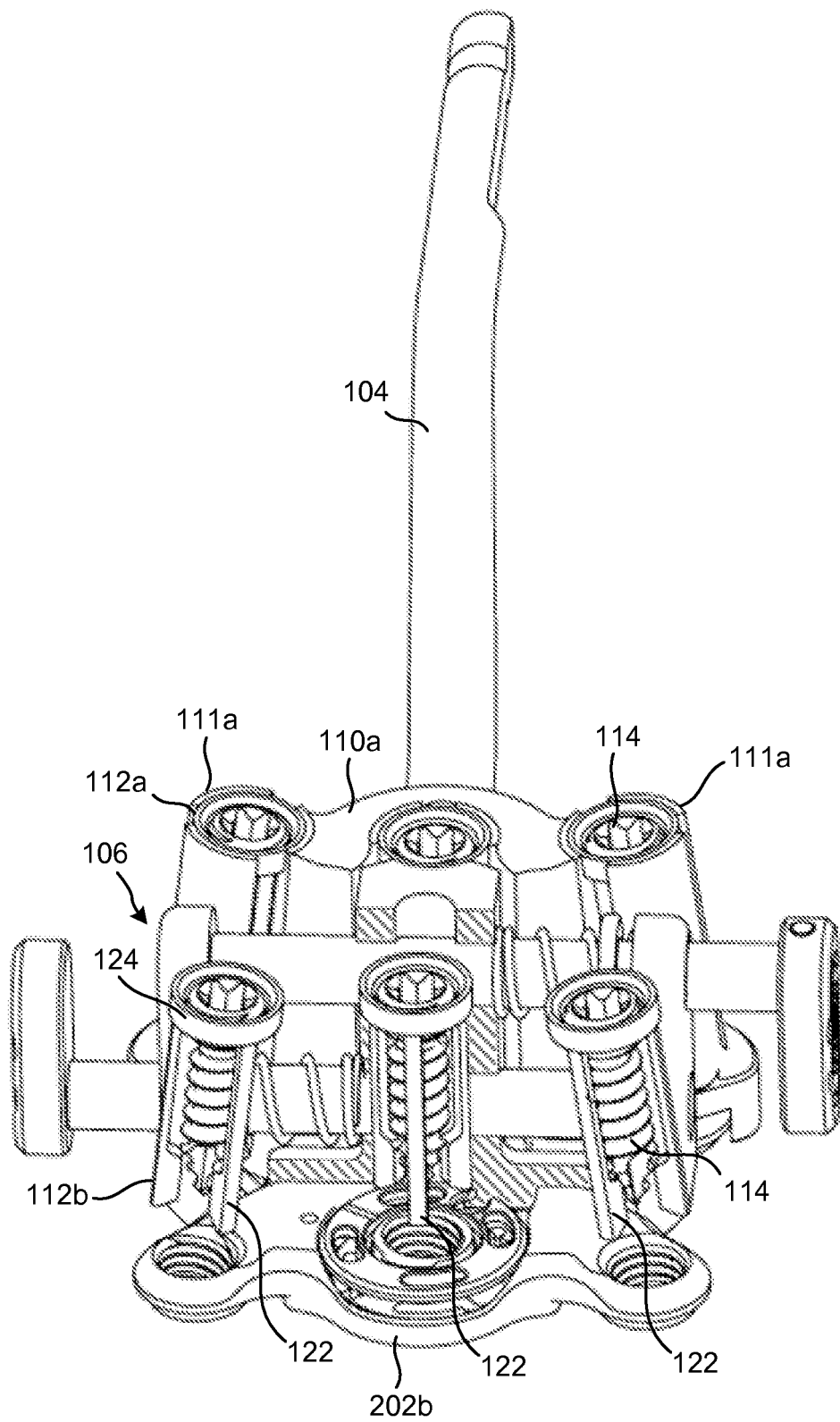
FIG. 5 illustrates a first cut-away view of the implant positioning device of FIG. 1 in accordance with an embodiment of the disclosure.
Figure 6:
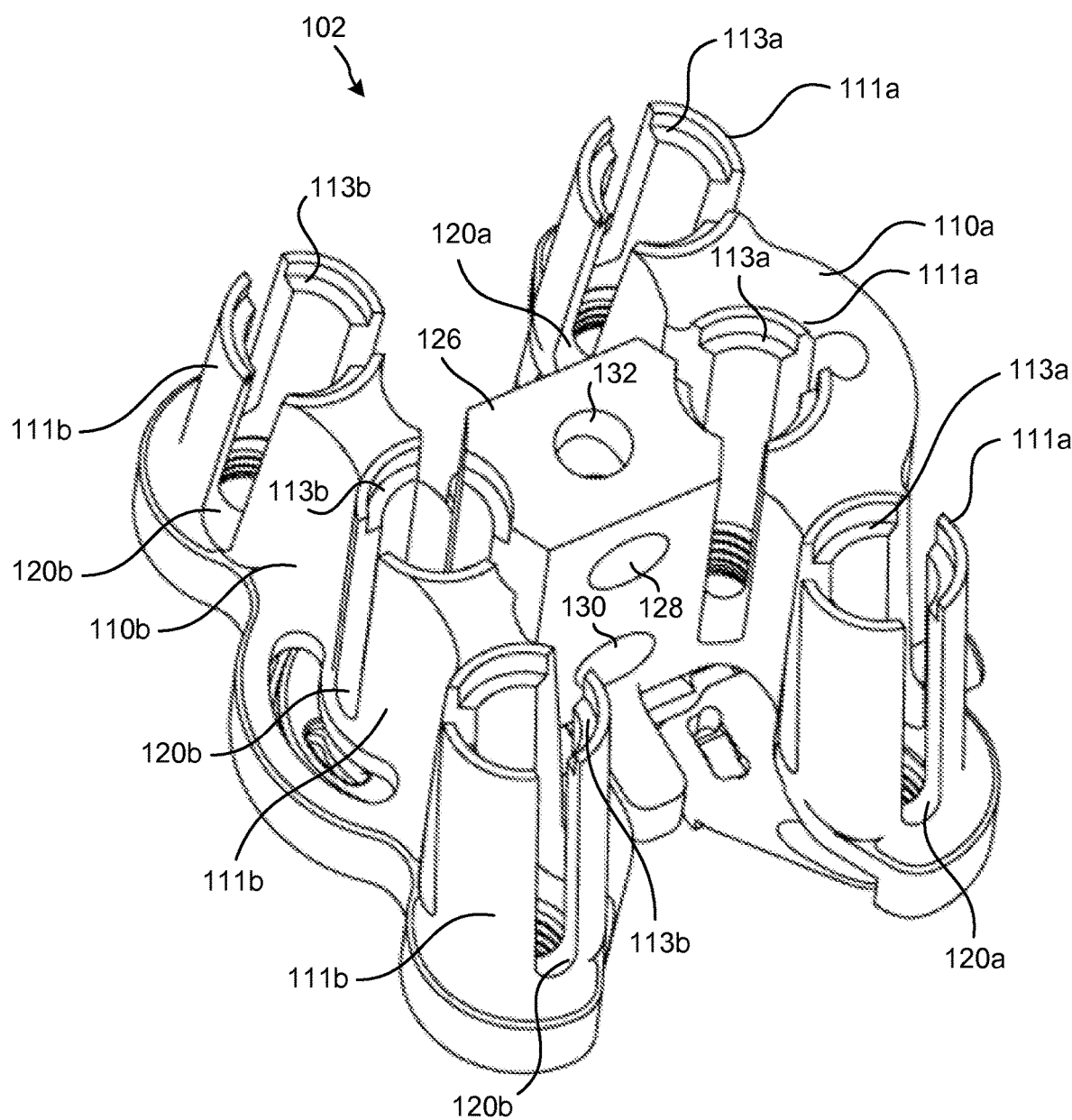
FIG. 6 illustrates a third perspective view of the body portion of the implant positioning device of FIG. 1 in accordance with an embodiment of the disclosure.
Figure 7:
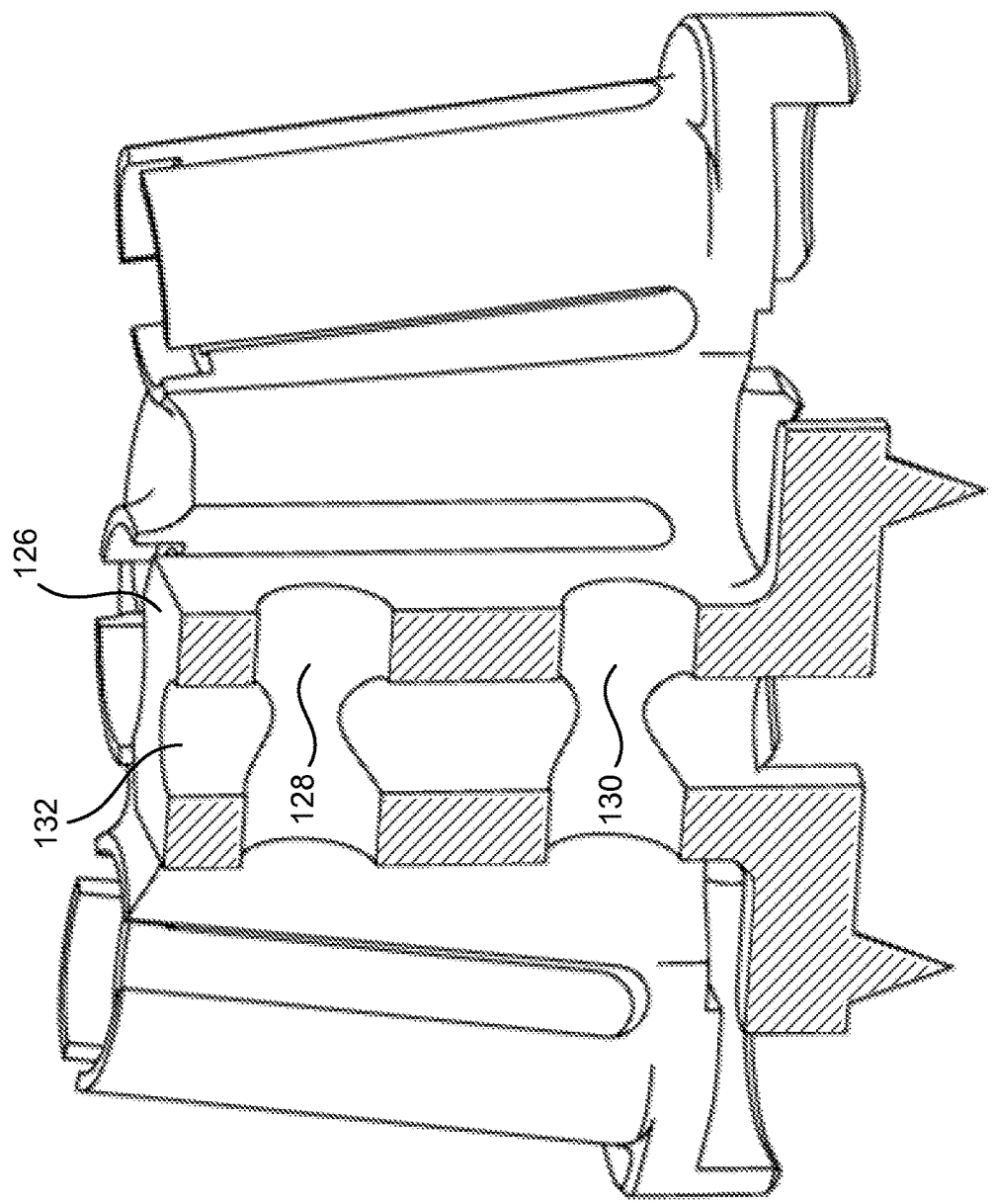
FIG. 7 illustrates a first cut-away view of the body portion of the implant positioning device of FIG. 1 in accordance with an embodiment of the disclosure.
Figure 8:
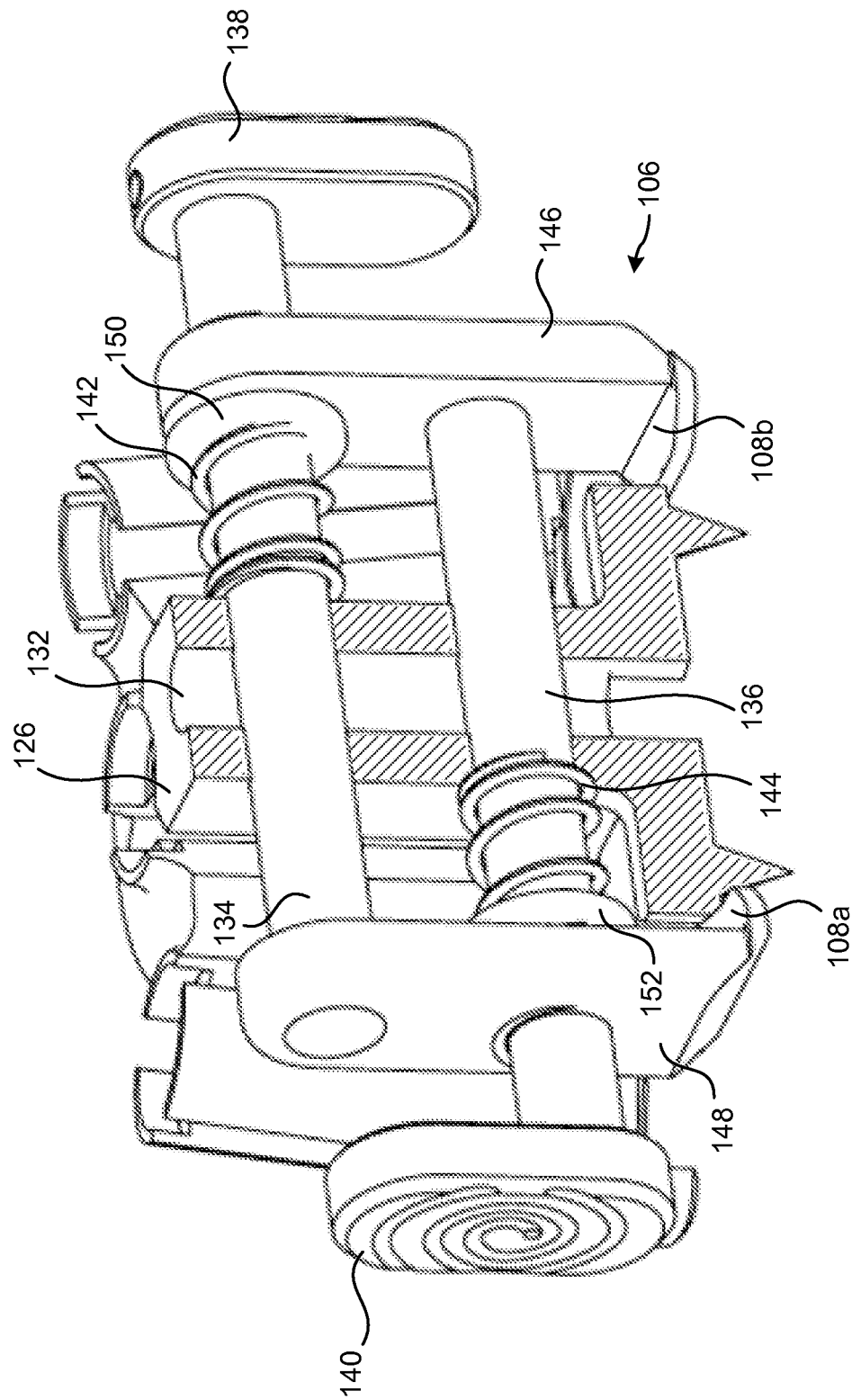
FIG. 8 illustrates a first cut-away view of the body portion of the implant positioning device of FIG. 1 showing a compression attachment mechanism in accordance with an embodiment of the disclosure.
Figure 9:
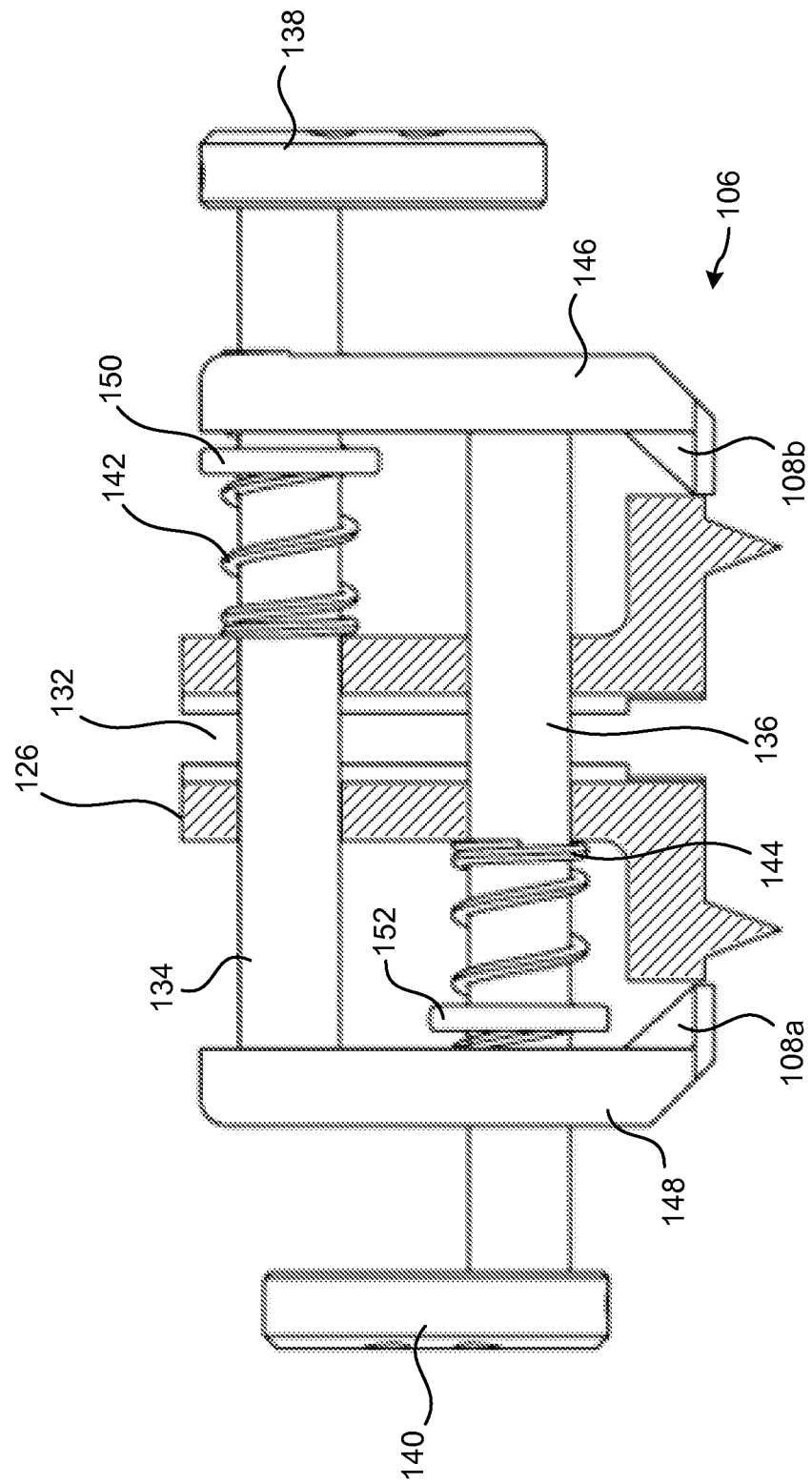
FIG. 9 illustrates a side cut-away view of the body portion of the implant positioning device of FIG. 1 showing the compression attachment mechanism in accordance with an embodiment of the disclosure.

Referring to FIGS. 1 and 5, the fastener captive elements 112a and 112b retain a fastener 114 in the respective fastener housings 111a and 111b of the first and second sets of fastener guides 110a and 110b. However, in other aspects, the fastener housings 111a and 111b may have no such side apertures 120a/120b and the fastener captive elements 112a and 112b may be contained within the respective fastener housings 111a and 111b of the first and second sets of fastener guides 110*a* and 110*b*. In this aspect, one or more internal recesses may be formed in the respective fastener housings 111*a* and 111*b* of the first and second sets of fastener guides 110*a* and 110*b* to receive and serve as expansion zones for the fastener captive elements 112*a*/112*b*.

Figure 3:
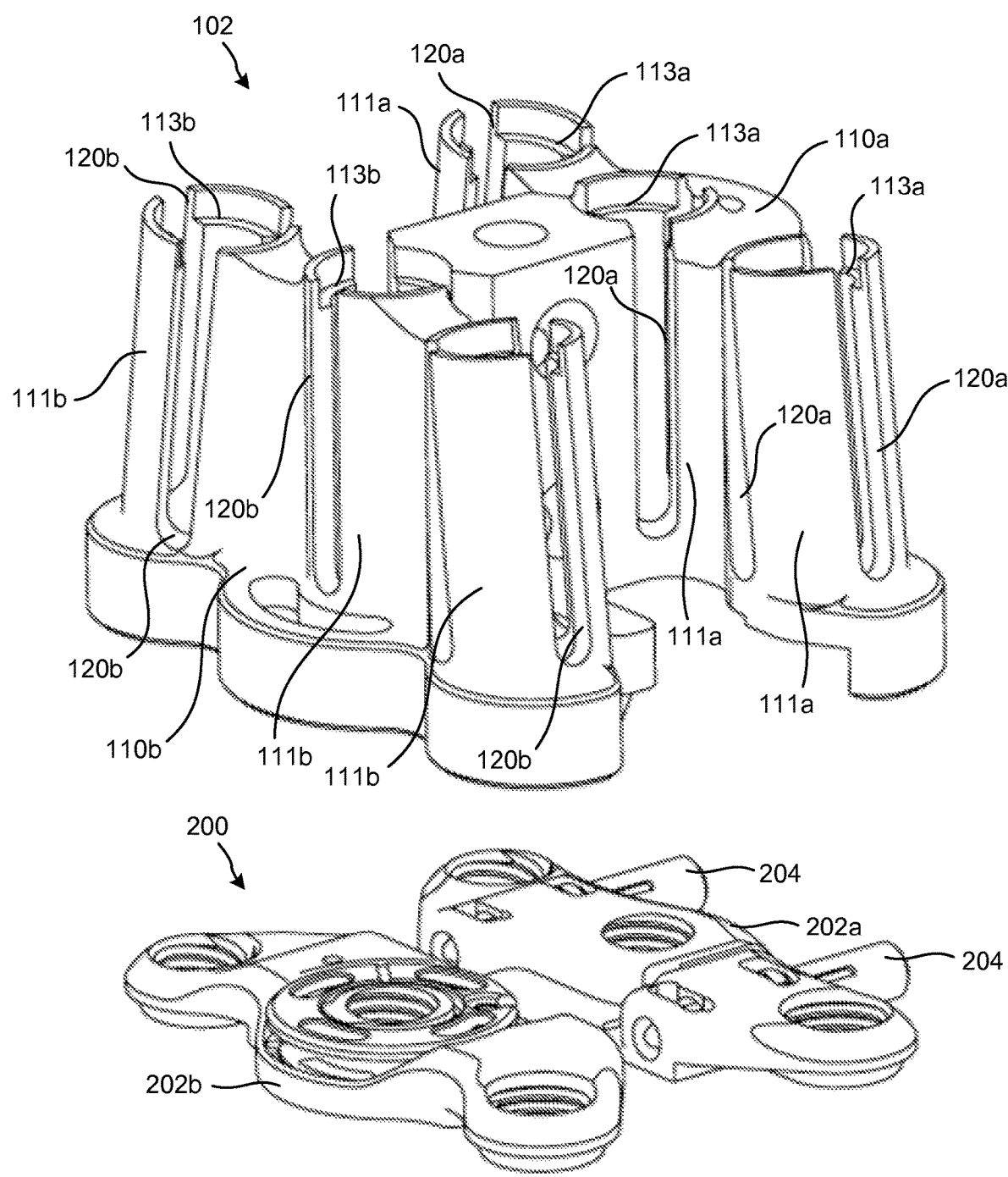
FIG. 3 illustrates a first perspective view of a body portion of the implant positioning device of FIG. 1 aligned with a pair of plates in accordance with an embodiment of the disclosure.
Figure 4:
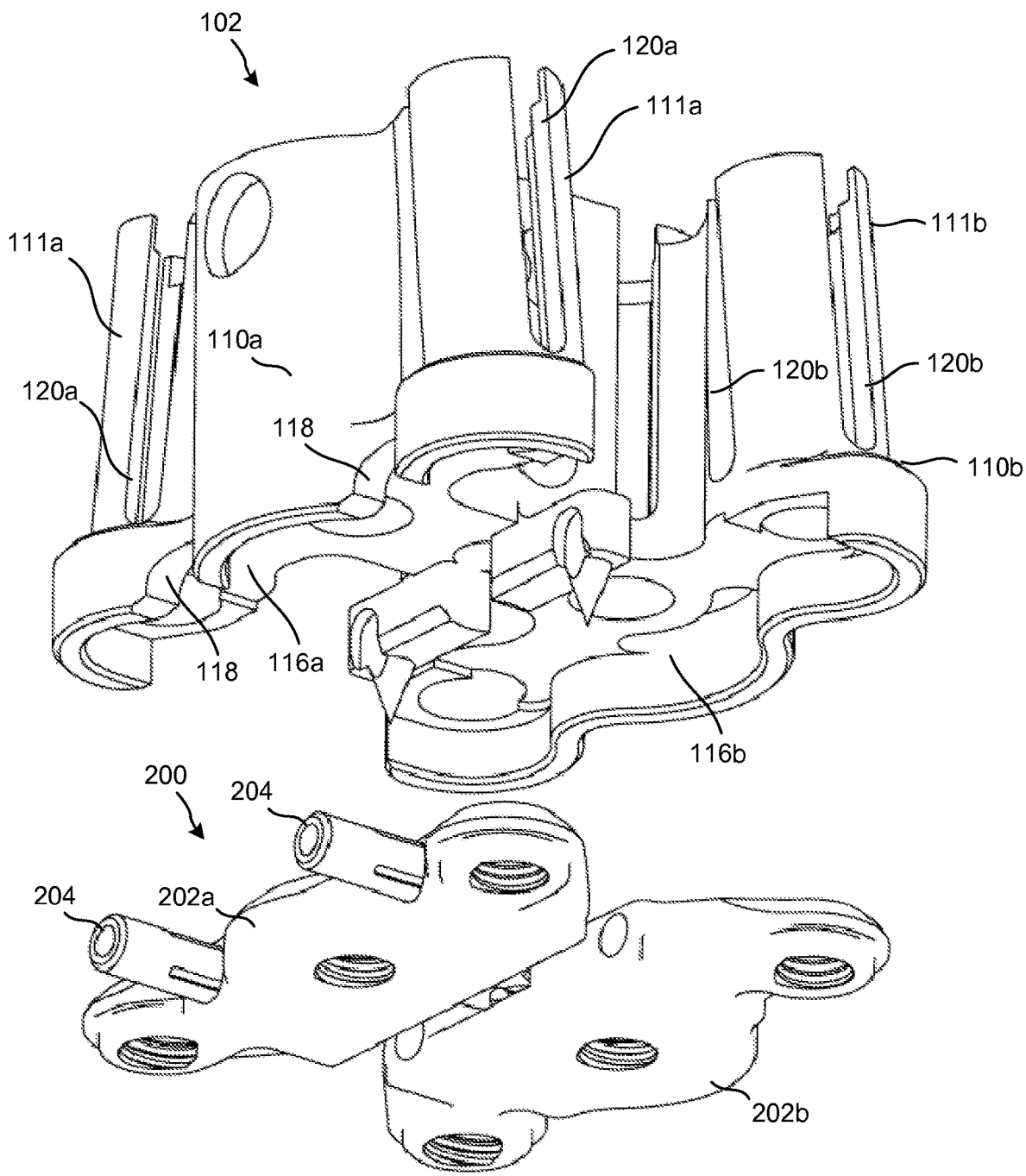
FIG. 4 illustrates a second perspective view of the body portion of the implant positioning device of FIG. 1 aligned with the pair of plates in accordance with an embodiment of the disclosure.

Referring to FIGS. 1, 3, and 5, the fastener captive elements 112*a* and 112*b* may be spring elements that create tension against the fastener 114 (for example, the threads of the fastener 114) and center the fastener 114 in the respective fastener housings 111*a* and 111*b* of the first and second sets of fastener guides 110*a* and 110*b*. As illustrated, each fastener captive element 112*a*, 112*b* includes three spring elements or prongs 122 extending downwardly from an upper collar 124. The prongs 122 extends along a side of fastener housing 111*a*, 111*b* and includes teeth that contact and grip a side of the fastener 114 (such as the threads of the fastener 114), and the collar 124 surrounds a head of the fastener 114 to hold the fastener 114 in the fastener captive element 112*a*, 112*b*. However, it should be appreciated that more or less than three prongs 122 may be used, and the fastener captive elements 112*a* and 112*b* may be cages, or other structure.

The prongs 122 may be located at various positions around each respective collar 124, for example, about 120 degrees apart, when there are three prongs 122. As illustrated, the fastener captive elements 112*a*, 112*b* center the fasteners 114 in the respective fastener housings 111*a* and 111*b* of the first and second sets of fastener guides 110*a* and 110*b* to ensure the fasteners 114 are deployed in a center of the corresponding apertures in the corresponding plate(s) 202*a*, 202*b*.

The fastener captive elements 112*a*, 112*b* serve as a capture mechanism. For example, fastener captive elements 112*a*, 112*b* are biased to compress against and apply a force to the fastener 114 and hold the fasteners 114 within each fastener housing 111*a* and 111*b*, respectively. Each fastener captive element 112*a* and 112*b* may be disposed in and removed from the respective fastener housings 111*a* and 111*b* of the first and second sets of fastener guides 110*a* and 110*b* for ease of loading fasteners into the respective fastener housings 111*a* and 111*b*. For example, a fastener, such as fastener 114, may be disposed in a fastener captive element 112*b* and then the fastener captive element 112*b* along with the fastener 114 may be loaded into a corresponding fastener housing 111*b* of the second set of fastener guides 110*b*. Referring to FIG. 3, each of the fastener housings 111*a* and 111*b* respectively include shoulders 113*a* and 113*b* that receive and abut the collar 124 of the respective fastener captive elements 112*a*, 112*b* and prevent the fastener captive elements 112*a*, 112*b* from sliding or being forced into the fastener housings 111*a* and 111*b* when the fastener 114 is driven into a bone.

As a fastener 114 is driven into a bone or other material, the fastener captive elements 112*a*/112*b* may expand elastically as a head of the fastener having a larger diameter than a shank or threaded portion of the fastener passes through the respective fastener housings 111*a* and 111*b*. Each of the fasteners 114 may have a head portion having a feature that mates with a driver (for example, a flat head, cross head, hex head etc. of a driver and/or drill) for use in insertion and receiving torque to drive the fasteners 114 into a bone or other body part. The fastener captive elements 112*a*/112*b* then return to their normal resting state for repeated use. The fastener captive elements 112*a*/112*b* also hold the fasteners 114 within each fastener housings 111*a* and 111*b* and prevent the fasteners 114 from accidentally falling out of the fastener housings 111*a* and 111*b* onto an operating room floor or into a patient's open body cavity.

Referring to FIGS. 6-10, the body 102 includes a central mounting structure 126 adapted to receive the compression attachment mechanism 106. As illustrated in FIGS. 6-9, the central mounting structure 126 couples the first and second sets of fastener guides 110*a* and 110*b* together and includes a first aperture 128 extending horizontally through the central mounting structure 126 and a second aperture 130 extending horizontally through the central mounting structure 126. The first aperture 128 is proximal to a top of the central mounting structure 126 and the second aperture 130 is proximal to a bottom of the central mounting structure 126. The central mounting structure 126 may also include a third aperture 132 extending vertically through the central mounting structure 126. This third aperture 132 may provide for easy cleaning and sterilization of the implant positioning device 100.

Figure 10:
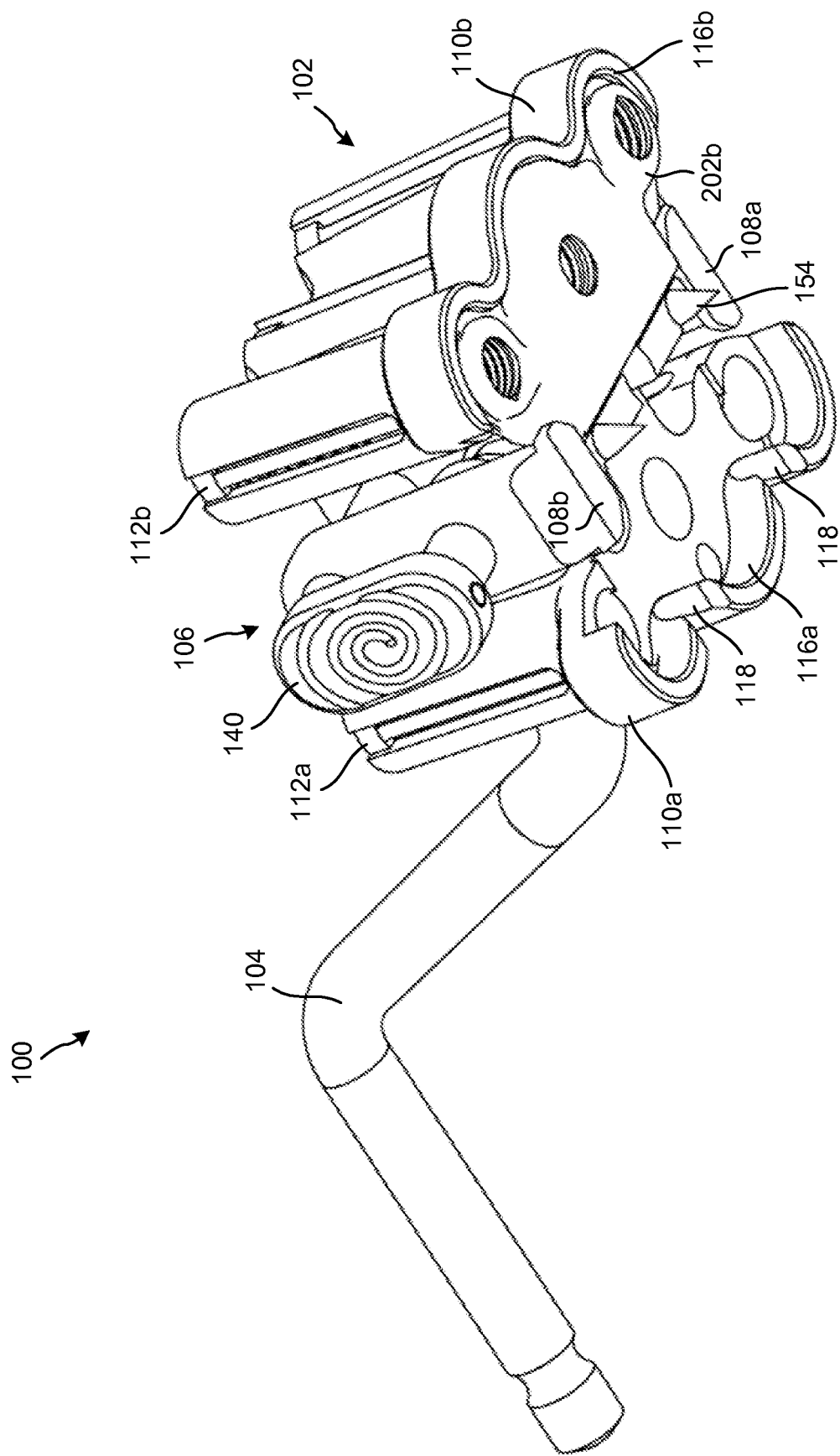
FIG. 10 illustrates a perspective view of the implant positioning device of FIG. 1 coupled with a plate in accordance with an embodiment of the disclosure.

The compression attachment mechanism 106 may be a spring loaded mechanism, that when compressed causes a distance between the attachment feet 108*a* and 108*b* to increase and when released causes the distance between the attachment feet 108*a* and 108*b* to decrease and mate with corresponding structure on the plate(s) 200 (as illustrated in FIG. 10). The attachment feet 108*a* and 108*b* serve to hold two plate halves (such as plates 202*a* and 202*b*) in the implant positioning device 100 at a predetermined distance from each other. As illustrated, the attachment feet 108*a* and 108*b* hold the two plate halves (such as plates 202 and 202*b*) in a coplanar arrangement, with the fastener apertures in the plate(s) aligned with the respective fastener housings 111*a* and 111*b* of the first and second sets of fastener guides 110*a* and 110*b*. Additionally or alternatively, the implant positioning device 100 may have clamping or connectable features in a plane opposite the attachment feet 108*a* and/or 108*b*, such as another set of feet oriented about 90 degrees from the attachment feet 108*a* and/or 108*b*. These feet may also thread into holes or attach in a number of different ways to plates and other devices.

The compression attachment mechanism 106 allows for the implant positioning device 100 to be coupled to and uncoupled from the plates 200 quickly and easily, simply by compressing the spring loaded mechanism. For example, referring to FIGS. 8-10, the compression attachment mechanism 106 may include one or more rails, such as a first rail 134 and a second rail 136 having corresponding gripping portions 138 and 140 and first and second springs 142 and 144 disposed on a corresponding rails 134 and 136.

The first rail 134 is disposed through a first support 146 of the compression attachment mechanism 106, through the first aperture 128 in the central mounting structure 126, and coupled to a second support 148 of the compression attachment mechanism 106. The first spring 142 is disposed on the first rail 134 between the first support 146 and the central mounting structure 126. A first stop 150 may also be disposed on the first rail 134 between the first spring 142 and the first support 146. As the first gripping portion 138 is depressed in a direction towards the second support 148, the first spring 142 is compressed and first rail 134 moves the second support 148, as well as the attachment feet 108*a* away from the attachment feet 108*b*.

In a similar manner, the second rail 136 is disposed through the second support 148 of the compression attachment mechanism 106, through the second aperture 130 in the central mounting structure 126, and coupled to the first support 146 of the compression attachment mechanism 106. The second spring 144 is disposed on the second rail 136 between the second support 148 and the central mounting structure 126. A second stop 152 may also be disposed on the second rail 136 between the second spring 144 and the second support 148. As the second gripping portion 140 is depressed in a direction towards the first support 146, the second spring 144 is compressed and the second rail 136 moves the first support 146, as well as the attachment feet 108b away from the attachment feet 108a.

Thus, when the gripping portions 138 and 140 are compressed in a direction towards one another, the distance between the feet 108a and 108b is increased. This allows the plates 200 to be placed in the implant positioning device 100, and when the compression force applied to the gripping portions 138 and 140 is released, the distance between the feet 108a and 108b decreases and the feet 108a and 108b mate with corresponding recesses on the plate(s) 200 to couple the plate(s) 200 to the implant positioning device 100 (for example as illustrated in FIG. 10). Other means and ways to hold a plate in place will also be readily adoptable.

As illustrated in FIGS. 2, 4, and 7-10, the implant positioning device 100 may also include one or more spikes 154 extending from a bottom of the body 102 of the implant positioning device 100 to assist in placing and holding the implant positioning device 100 and the plate(s) 200 in a proper orientation as the fasteners 114 are driven to couple the plate(s) 200 to a bone or other portion of a patient's body.

A grip may also be removably coupled to the handle 104 to provide for ease of use of the implant positioning device 100. The handle 104 may be used to retain the implant positioning device 100 in a particular position for ease of assembly of elements (such as the plates 200) that may be connected to it. As illustrated, the implant positioning device 100 may be coupled to the plates 200 having fastener holes and various other features. The handle 104 and grip may have an ergonomic design for comfort and control of the implant positioning device 100. The handle 104 may also be angled to accommodate soft tissues and various surgical approaches. Further, the handle 104 may be removable from the body 102.

In another embodiment, an implant positioning device 300 is described with reference to FIGS. 11-15. The implant positioning device 300 is similar to the implant positioning device 100 described above, but includes the modifications as described below. For example, the implant positioning device 300 includes a body 302 and a compression attachment mechanism 306 including attachment feet 308a and 308b.

The body 302 includes one or more sets of fastener guides (for example, a first set of fastener guides 310a and a second set of fastener guides 310b) disposed on opposite sides of the body 302 and having respective fastener captive elements 312a and 312b disposed in respective first and second fastener housings 311a and 311b. The first and second sets of fastener guides 310a and 310b provide fastener housings 311a and 311b to guide fasteners (such as fasteners 114 described above) for insertion into fastener apertures in one or more plates (such as plates 200, including the first plate 202a and the second plate 202b) to install the plate(s) on bone or other area of a patient. As illustrated, there are two sets (the first and second sets of fastener guides 310a and 310b, one on each side of the body 302), each having three fastener housings 311a, 311b. However, there may be more or less than three fastener housings in each of the first and second sets of fastener guides 310a and 310b and the fasteners may be pins, rivets, and other types of fasteners, etc.

Figure 11:
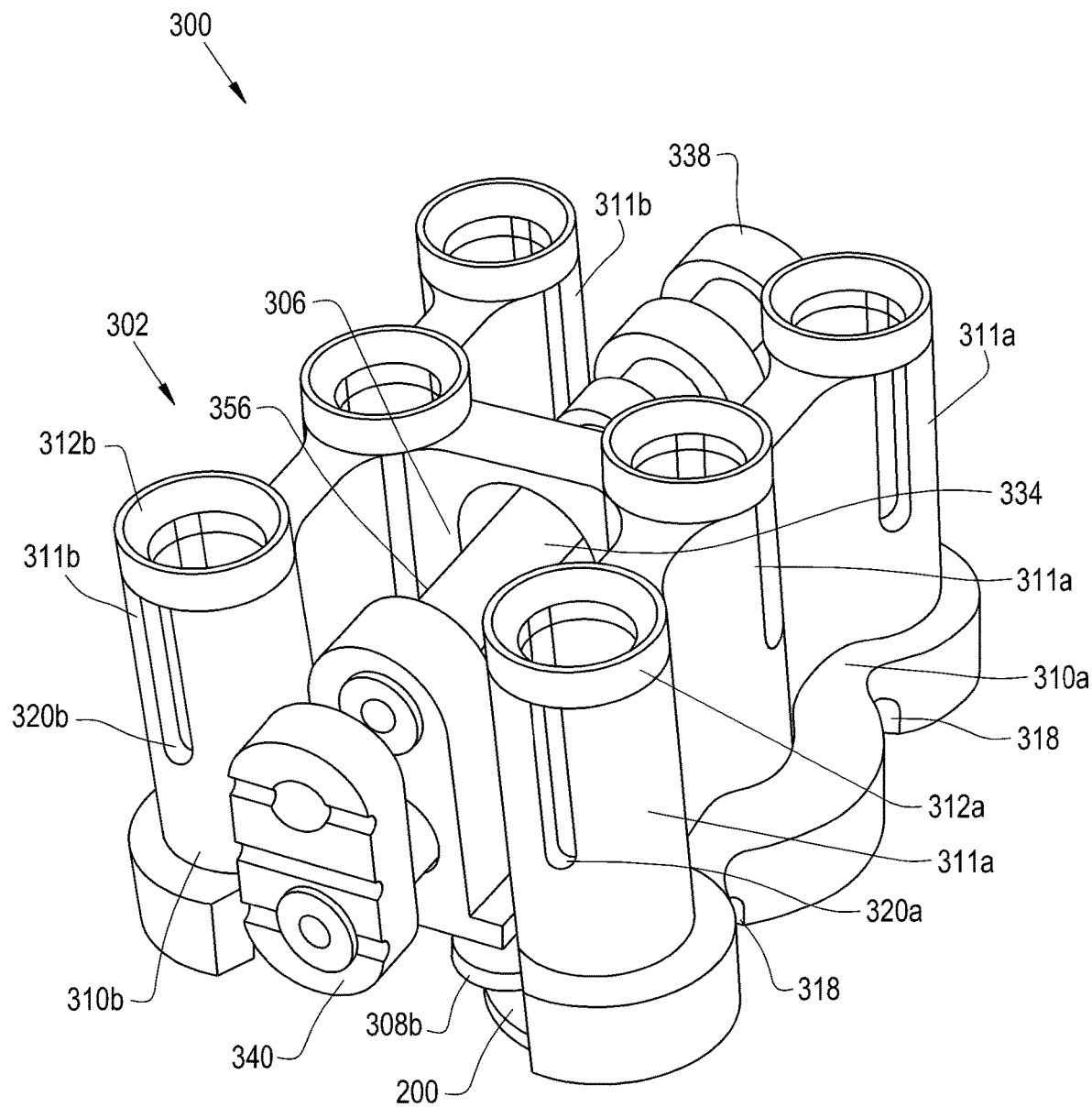
FIG. 11 illustrates a perspective view of another implant positioning device in accordance with an embodiment of the disclosure.

The first and second fastener housings 311a, 311b communicate with respective first and second recesses 316a and 316b in a bottom of the body 302. The respective first and second recesses 316a and 316b are respectively sized and shaped to receive the corresponding first and second plates 202a and 202b. As described above, the first plate 202a includes shear bars or pins 204. In this respect, the first sets of fastener guides 310a includes grooves 318 (as illustrated in FIG. 11) that communicate with the first recess 316a and receive the corresponding pins 204 when the first plate 202a is received in the first recess 116a and the pins 204 are in an undeployed position.

As described above, each of the first and second fastener housings 311a, 311b may be cylindrical hollow tube like guide barrels that are positioned and oriented to align with the fastener apertures in the plate(s). While the first and second fastener housings 311a and 311b are illustrated as positioned and oriented to align with the fastener apertures of the plate(s) 200, the first and second sets of fastener guides 310a and 310b and/or the individual guide barrels may be positioned and oriented to align with apertures of any plate or other device.

As described above with reference to the implant positioning device 100, the first and second sets of fastener guides 310a and 310b of the implant positioning device 300 may also be used to guide a driver and/or drill depending on the application, and/or to guide other instruments, for example, to place markings, pegs, headless pins, etc. in a bone, which then serve as locating features to place plates or any other device after a resection is made. The implant positioning devices may also be used simply to apply fasteners or other fixation elements alone, or in a desired pattern, as for use in a wired closure arrangement.

The first and second sets of fastener guides 310a and 310b may be disposable, and pre-loaded with fasteners. For example, the first and second sets of fastener guides 310a and 310b may be removable from the compression attachment mechanism 306. This allows the first and second sets of fastener guides 310a and 310b to be easily replaced during a surgical procedure. For example, the first and second sets of fastener guides 306a and 306b may be coupled around at least a portion of the compression attachment mechanism 306 (such as a housing 356) due to the shape of the first and second sets of fastener guides 310a and 310b and the first and second sets of fastener guides 310a and 310b may be coupled together by pins, for example.

As illustrated, each of the first and second fastener housings 311a and 311b of the first and second sets of fastener guides 310a and 310b include one or more side apertures or slits 320a and 320b, respectively, that receive and serve as expansion zones for the respective fastener captive elements 312a and 312b for retaining a fastener in a corresponding first and second fastener housing 311a, 311b of the first and second sets of fastener guides 310a and 310b. However, in other aspects, the first and second fastener housings 311a, 311b of the first and second sets of fastener guides 310a and 310b may have no such side apertures 320a/320b and the fastener captive elements 312a/312b may be contained within the respective first and second fastener housings 311a, 311b. In this aspect, one or more internal recesses may be in the first and second fastener housings 311a, 311b to receive and serve as expansion zones for the respective fastener captive elements 312a/312b.

Figure 13:
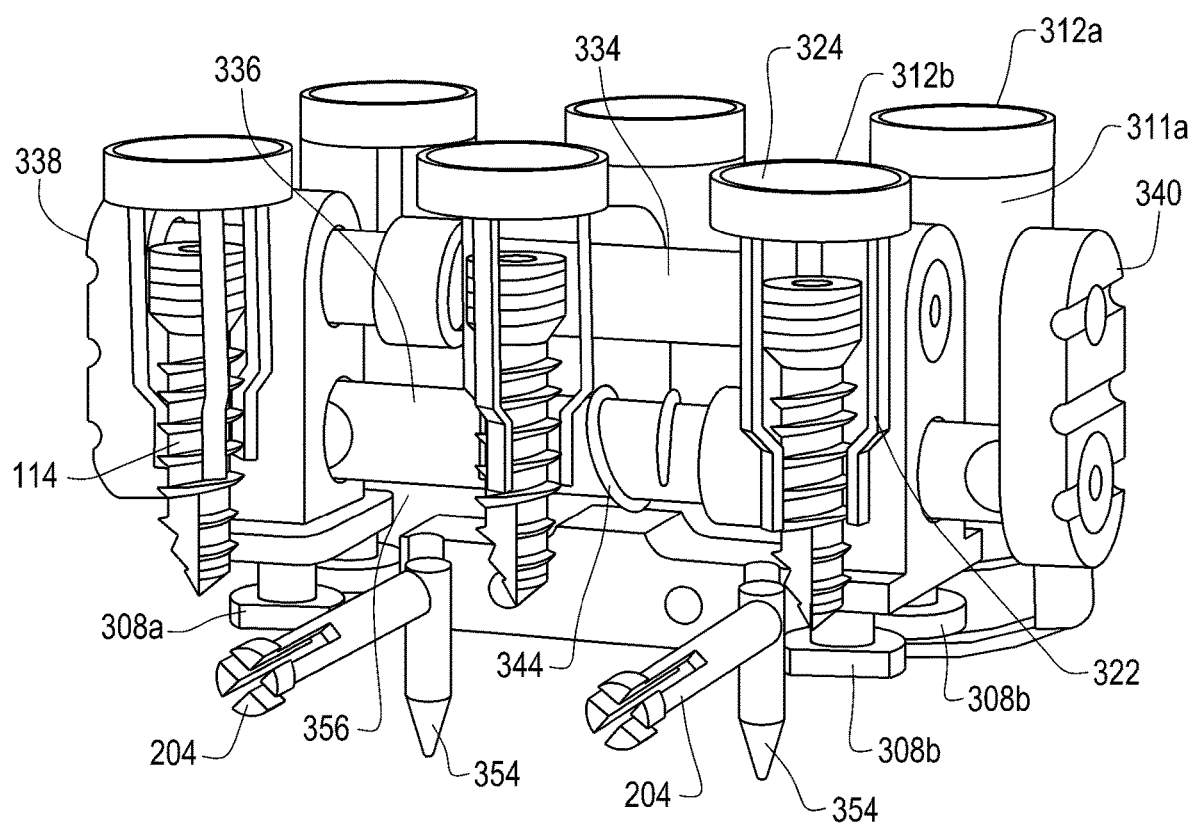
FIG. 13 illustrates a first cut-away view of the body portion of the implant positioning device of FIG. 11 showing fasteners in accordance with an embodiment of the disclosure.

The fastener captive elements 312a and 312b may be spring elements that create tension against the fastener 114 (for example, the threads of the fastener) and center the fastener 114 in the respective first and second fastener housings 311a, 311b. As illustrated in FIG. 13, each fastener captive element 312a and 312b includes three spring elements coupled to an upper collar. For example, each fastener captive element 312a and 312b includes three spring elements 322 coupled to an upper collar 324. However, it should be appreciated that more or less than three spring elements may be used.

Each fastener captive element 312a and 312b may be disposed in and removed from the respective first and second fastener housing 311a, 311b for ease of loading fasteners into the respective first and second fastener housing 311a, 311b. For example, a fastener, such as fastener 114, may be disposed in a fastener captive element 312b and then the fastener captive element 312b along with the fastener 114 may be loaded into a corresponding fastener housing 311b of the second set of fastener guides 310b.

The fastener captive elements 312a and 312b serve to center the fasters in the respective first and second fastener housings 311a, 311b of the first and second sets of fastener guides 310a and 310b and serve also as a capture mechanism. For example, the spring elements 322 compress against and apply a force to the fastener 114 and hold the fasteners 114 within each first and second fastener housings 311a, 311b. As a fastener 114 is driven out of a first and second fastener housing 311a, 311b and into a bone or other material, the spring elements 322 may expand elastically as a head of the fastener having a larger diameter than a shank or threaded portion of the fastener passes through the first and second fastener housing 311a, 311b. The spring elements 322 then return to their normal resting state for repeated use. The fastener captive elements 312a, 312b also hold the fasteners 114 within the respective first and second fastener housings 311a, 311b of the first and second sets of fastener guides 310a and 310b and prevent the fasteners 114 from accidentally falling out of the first and second fastener housings 311a, 311b onto an operating room floor or into a patient's open body cavity.

The compression attachment mechanism 306 may include a spring loaded mechanism that when compressed causes a distance between the attachment feet 308a and 308b to increase and when released causes the distance between the attachment feet 308a and 308b to decrease and mate with corresponding structure (such a mating recesses) in the plate(s) 200. The attachment feet 308a and 308b serve to hold the two plate halves 202a and 202b in the implant positioning device 300 at a predetermined distance from each other. As described above, the attachment feet 308a and 308b hold the plate halve(s) 202a and 202b in a coplanar arrangement, with the fastener apertures in the plate(s) 202a and 202b aligned with the respective guide barrels of the first and second sets of fastener guides 310a and 310b.

The compression attachment mechanism 306 allows for the implant positioning device 300 to be coupled to and uncoupled from the plate(s) quickly and easily, simply by compressing the spring loaded mechanism. For example, referring to FIGS. 11-15, the compression attachment mechanism 306 may include a housing 356, one or more rails 334 and 336 having corresponding gripping portions 338 and 340 and springs 342 (not shown) and 344 disposed on a corresponding rail 334 or 336. It should be appreciated that the housing 356 is illustrated in FIGS. 14-15 as transparent to allow an internal structure of the compression attachment mechanism 306 to be visible.

Figure 14:
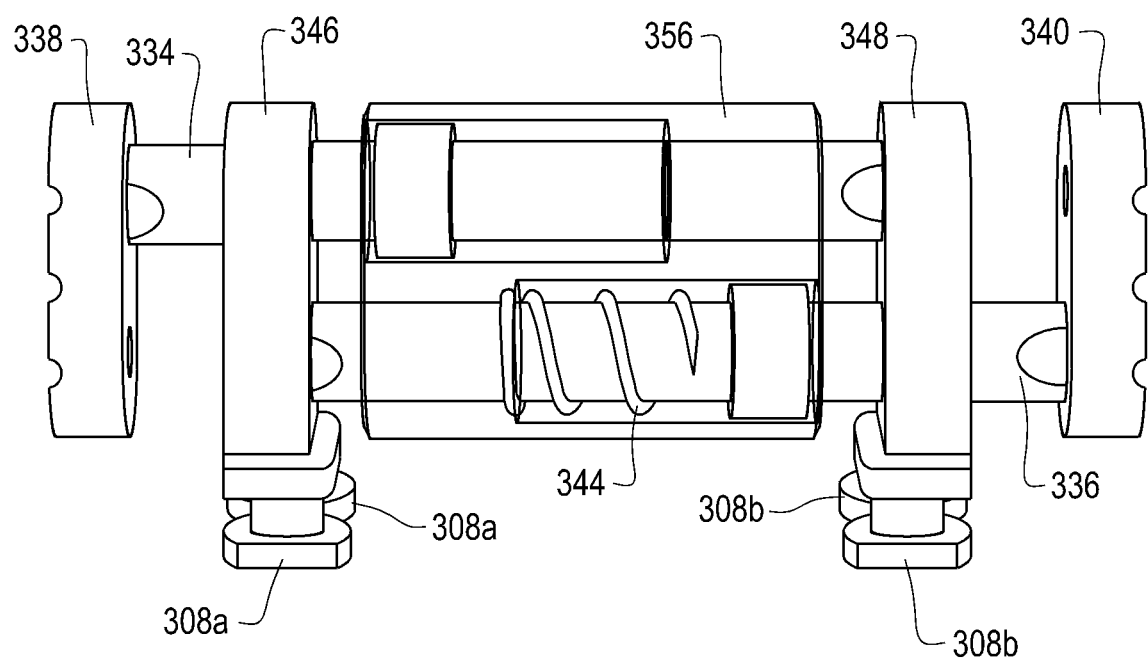
FIG. 14 illustrates a perspective view of the compression attachment mechanism of the implant positioning device of FIG. 11 in accordance with an embodiment of the disclosure.

Referring to FIG. 14, the compression attachment mechanism 306 includes two rails, a top or first rail 334 and a bottom or second rail 336 below the first rail 334. The first rail 334 is disposed through a first support 346 and coupled to a second support 348, and the second rail 336 is disposed through the second support 348 and coupled to the first support 346. The housing 356 is disposed around the rails between the first support 346 and the second support 348.

Figure 15:
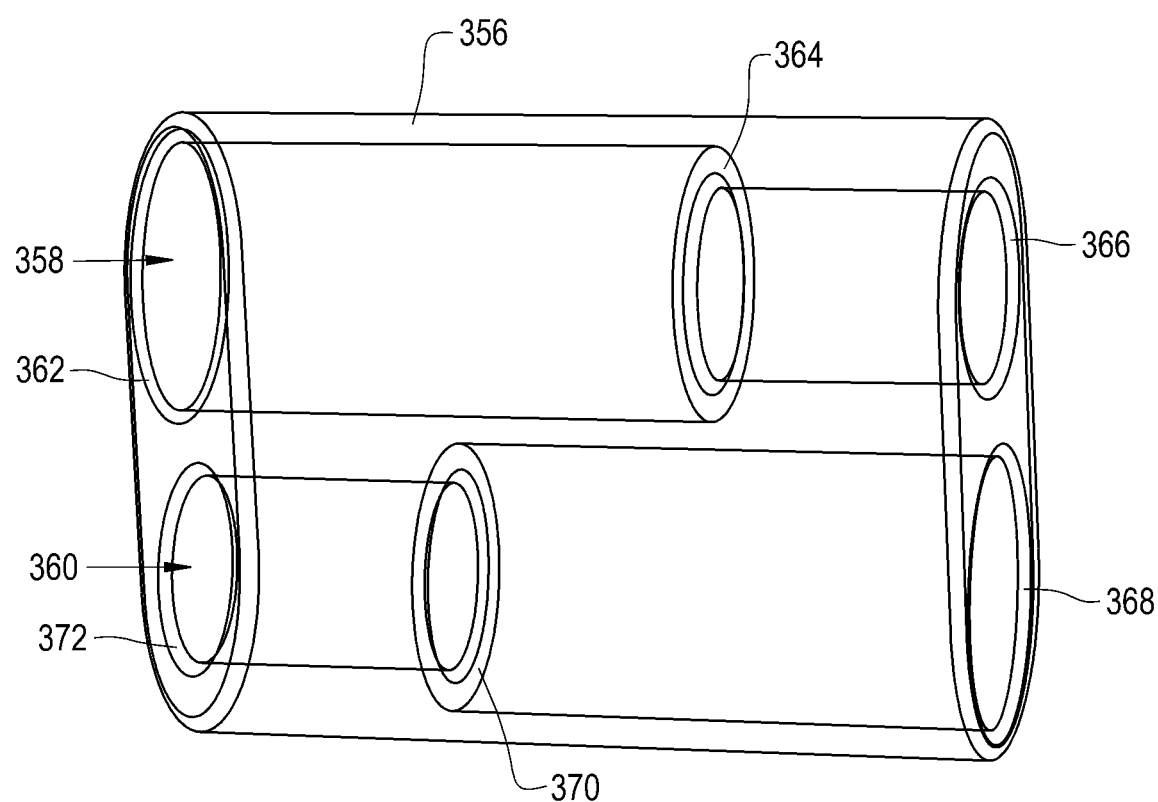
FIG. 15 illustrates a perspective view in phantom of a housing of the compression attachment mechanism of the implant positioning device of FIG. 11 in accordance with an embodiment of the disclosure.

Referring to FIGS. 14 and 15, the housing 356 includes a first longitudinal channel 358 adapted to receive the first rail 334 and a second longitudinal channel 360 adapted to receive the second rail 336. The first longitudinal channel 358 extends from a first opening 362 having a first diameter to a stop 364 internal to the housing 356, at which the first longitudinal channel 358 transitions to a second diameter smaller than the first diameter and continues to extend from the stop 364 to a second opening 366. Similarly, the second longitudinal channel 360 extends from a first opening 368 having a first diameter to a stop 370 internal to the housing 356, at which the second longitudinal channel 360 transitions to a second diameter smaller than the first diameter and continues to extend from the stop 370 to a second opening 372. As illustrated, the first opening 362 with the first diameter of the first longitudinal channel 358 is proximal to a first end of the housing 356, and the first opening 368 with the first diameter of the second longitudinal channel 360 is proximal to a second end of the housing 356 opposite the first end.

A spring is disposed around each of the rails 334 and 336, and positioned in the respective areas of the housing having the first diameter. As illustrated, only the spring 344 is illustrated as disposed around the second rail 336 and disposed in the first diameter of the second longitudinal channel 360. It should be appreciated that a similar spring is also disposed around the first rail 334 and disposed in the first diameter of the first longitudinal channel 358.

The spring 344 applies a spring bias force against the stop 370 where the transition of the first and second diameters is located in a direction of the gripping portion 140 of the second rail 336. Similarly, the spring of the first rail 334 applies a spring bias force against the stop 364 where the transition of the first and second diameters is located in a direction of the gripping portion 338 of the first rail 334. When the gripping portions 338 and 340 are compressed in a direction towards the housing 356 or one another, the distance between the feet 308a and 308b is increased. This allows the implant positioning device 300 to be placed over the plate(s) 200, and when the compression force applied to the gripping portions 330a and 340 is released, the distance between the feet 308a and 308b decreases and the feet 308a and 308b mate with the recesses on the plate(s) 200 to couple the plate(s) 200 to the implant positioning device.

Figure 12:
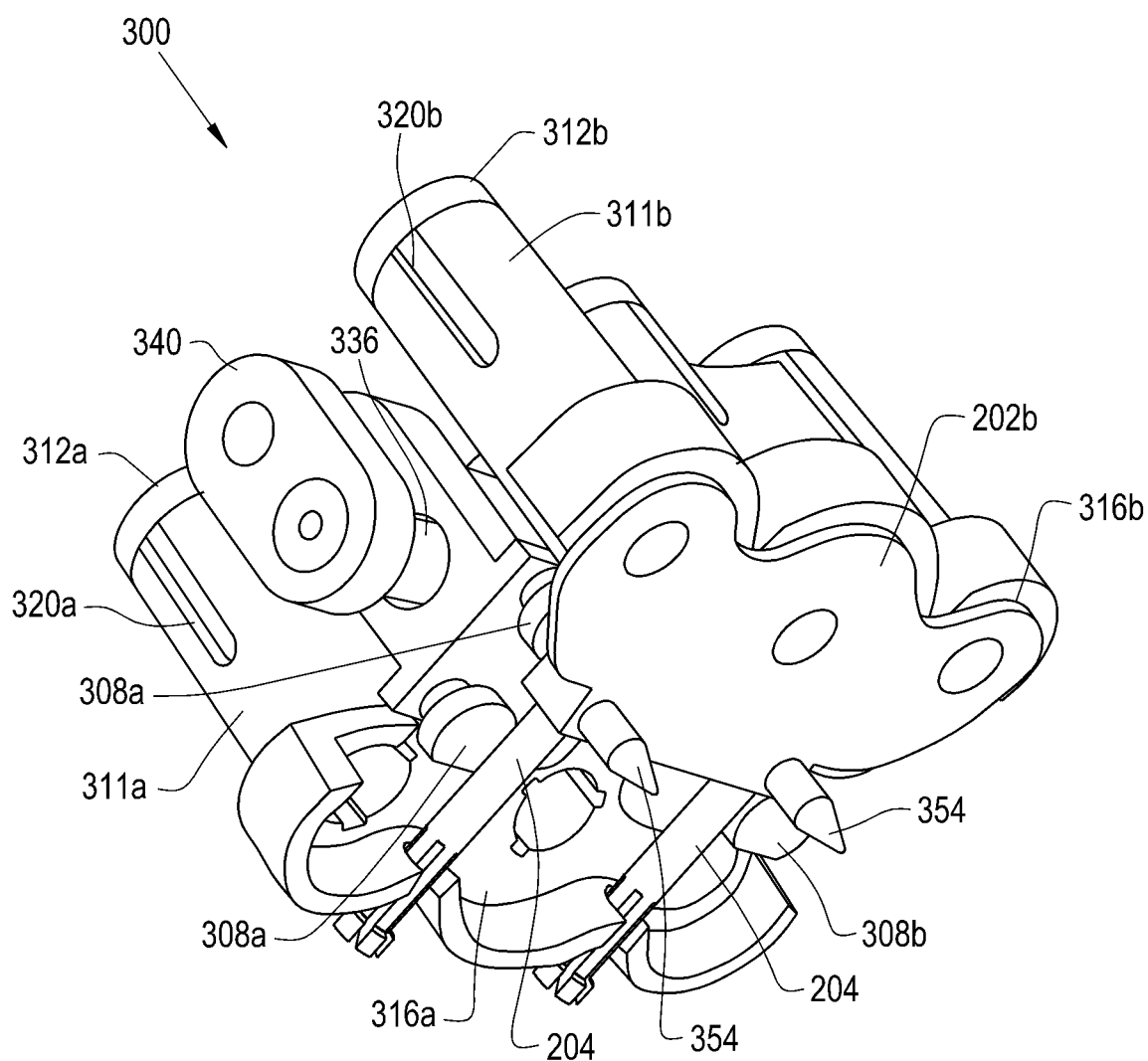
FIG. 12 illustrates a perspective view of the implant positioning device of FIG. 11 coupled with a plate in accordance with an embodiment of the disclosure.

As illustrated in FIGS. 12 and 13, the implant positioning device 300 may also include one or more spikes 354 extending from a bottom of the implant positioning device 300 to assist in placing and holding the implant positioning device 300 and the plate(s) 200 in a proper orientation as the fasteners 114 are driven to couple the plate(s) 200 to a bone or other portion of a patient's body.

Figure 16:
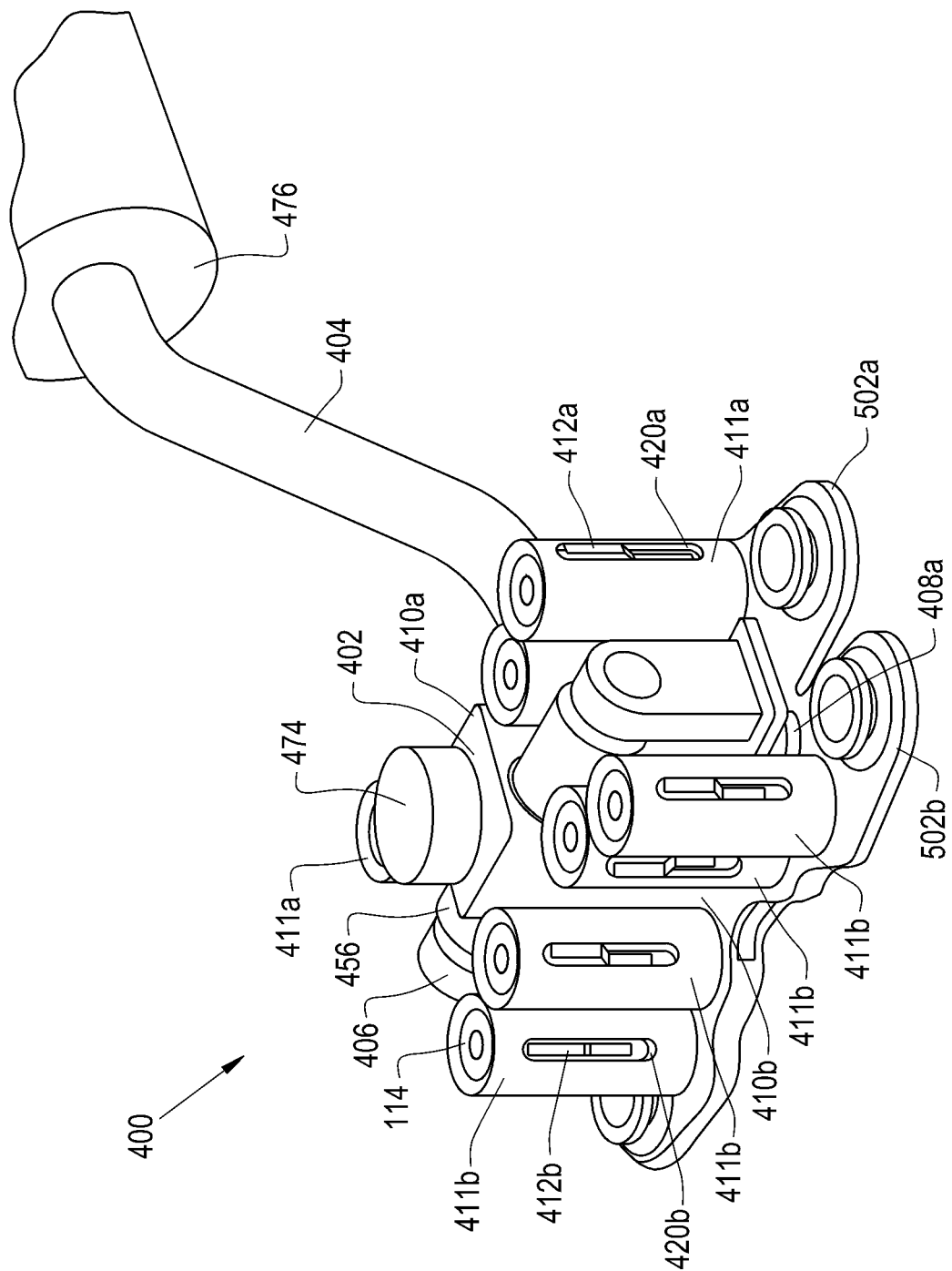
FIG. 16 illustrates a perspective view of another implant positioning device of in accordance with an embodiment of the disclosure.
Figure 17:
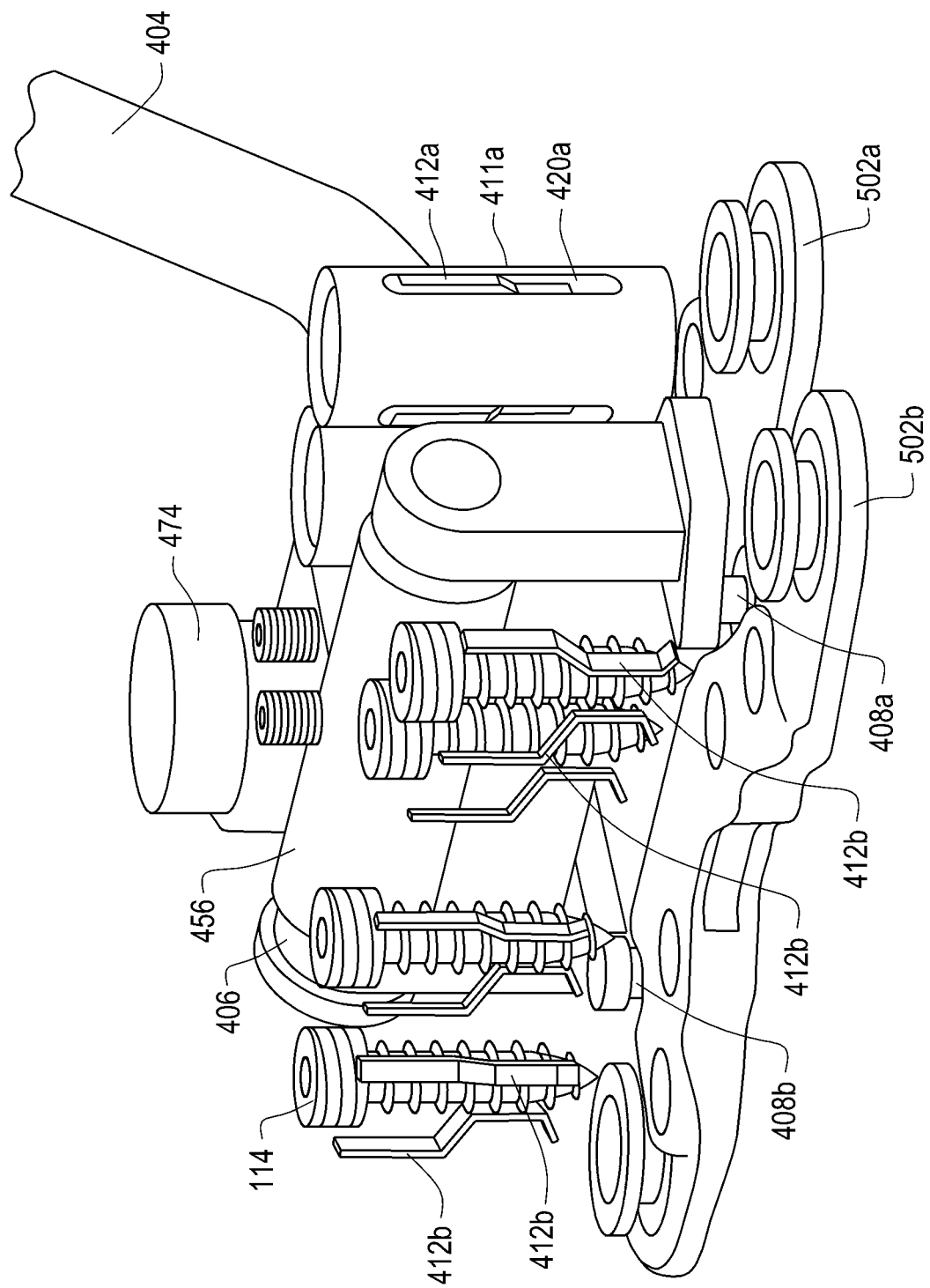
FIG. 17 illustrates a first cut-away view of the body portion of the implant positioning device of FIG. 16 showing fasteners in accordance with an embodiment of the disclosure.

In yet another embodiment, an implant positioning device 400 is described with reference to FIGS. 16 and 17. The implant positioning device 400 is similar to the implant positioning devices 100 and 300 described above, but includes the modifications as described below. For example, the implant positioning device 400 includes a body 402, a handle 404 coupled to the body 402, and a compression attachment mechanism 406 including attachment feet 408a and 408b.

The body 402 includes one or more sets of fastener guides (for example, a first set of fastener guides 410a and a second set of fastener guides 410b) disposed on opposite sides of the body 402 and having respective first and second fastener housings 411a and 411b that receive corresponding fastener captive elements 412a and 412b.

The first and second sets of fastener guides 410a and 410b provide fastener housings 411a and 411b to hold and guide fasteners 114 for insertion into and through fastener apertures in one or more plates 500 (including first and second plates 502a and 502b) to install the plate(s) on a bone or other area of a patient. As illustrated, there are two sets, the first and second sets of fastener guides 410a and 410b, (one disposed on each side of the body 402), with each set including four fastener housings 411a, 411b. However, there may be more or less than four fastener housings in each set of fastener guides and the fasteners may be pins, rivets, and other types of fasteners, etc.

In this embodiment, the first and second sets of fastener guides 410a and 410b provide fastener housings 411a and 411b in the form of substantially cylindrical, hollow, tube like guide barrels that are positioned to align with the fastener apertures in the plate(s). While the first and second sets of fastener guides 410a and 410b are illustrated as positioned to align with the fastener apertures of the plate(s) 502a and 502b, the first and second sets of fastener guides 410a and 410b may be positioned to align with apertures of any plate(s) or other device, and/or the location of the guides in each of the first and second sets of fastener guides 410a and 410b may be adapted or modified to align with apertures of any plate(s) or other device.

As described above, the first and second sets of fastener guides 410a and 410b may also be used to guide a driver, drill, or instrument depending on the application, for example, to place markings, pegs, headless pins, etc. in a bone, which then serve as locating features to place plates or any other device before or after a resection is made.

In an aspect, the individual fastener housings 411a and 411b of the first and second sets of fastener guides 410a and 410b may be adapted to swivel to allow for varying degrees of angular positions for guiding the fasteners 114. In another aspect, the individual fastener housings 411a and 411b of the first and second sets of fastener guides 410a and 410b may individually be slidable along a shaft or bar to allow the position of each respective fastener housings 411a, 411b to be adjusted. A length and diameter of the individual fastener housings 411a and 411b of the first and second sets of fastener guides 410a and 410b may also be varied to accommodate different lengths of fasteners and fasteners of different diameters.

In an aspect, the first and second sets of fastener guides 410a and 410b may be disposable, and pre-loaded with fasteners. This allows the first and second sets of fastener guides 410a and 410b to be easily replaced during a surgical procedure. For example, the first and second sets of fastener guides 410a and 410b may be coupled to the compression attachment mechanism 406 by a compression locking mechanism 474 (which is illustrated as a turn knob). Removal of the compression locking mechanism 474 allows the first and second sets of fastener guides 410a and 410b to be removed from the compression attachment mechanism 406.

As illustrated, each of the fastener housings 411a and 411b of the first and second sets of fastener guides 410a and 410b include one or more side apertures, such as first side apertures 420a and second side apertures 420b. The first and second side apertures 420a and 420b receive and serve as expansion zones for the fastener captive elements 412a and 412b, respectively. The fastener captive elements 412a and 412b retain a fastener 114 in the respective fastener housing 411a, 411b of the first and second sets of fastener guides 410a and 410b. However, in other aspects, the fastener housings 411a and 411b may have no such side apertures 420a/420b and the fastener captive elements 412a and 412b may be contained within the respective fastener housing 411a and 411b. In this aspect, one or more internal recesses may be formed in the respective fastener housings 411a and 411b to receive and serve as expansion zones for the fastener captive elements 412a/412b.

The fastener captive elements 412a and 412b may be spring elements that create tension against the fastener 114 (for example, the threads of the fastener) and center the fastener 114 in the respective fastener housings 411a and 411b. As illustrated, there are three fastener captive elements 412a in each respective fastener housing 411a of the first set of fastener guides 410a, and three fastener captive elements 412b in each respective fastener housing 411b of the second set of fastener guides 410b. However, it should be appreciated that more or less than three may be used.

The fastener captive elements 412a, 412b may be located at various positions around each respective fastener housings 411a and 411b, for example, about 120 degrees apart, when there are three fastener captive elements 412a, 412b per fastener housing 411a, 411b. As illustrated, the fastener captive elements 412a, 412b center the fasteners 114 to ensure the fasteners 114 are deployed in a center of the corresponding apertures in the plate(s) 502a, 502b.

The fastener captive elements 412a, 412b also serve as a capture mechanism. For example, as a fastener 114 is driven into a bone or other material, the fastener captive elements 412a, 412b may expand elastically as a head of the fastener having a larger diameter than a shank or threaded portion of the fastener passes through the respective fastener housing 411a, 411b. The fastener captive elements 412a, 412b then return to their normal resting state for repeated use. The fastener captive elements 412a, 412b also hold the fasteners 114 within each fastener housing 411a, 411b and prevent the fasteners 114 from accidentally falling out of the fastener housings 411a, 411b onto an operating room floor or into a patient's open body cavity.

The compression attachment mechanism 406 (which is similar in construction to the compression attachment mechanism 106 and/or 306 described above) may include a spring loaded mechanism, disposed in the housing 456, that when compressed causes a distance between the attachment feet 408a and 408b to increase and when released causes the distance between the attachment feet 408a and 408b to decrease and mate with corresponding structure on the plate(s). As illustrated, the attachment feet 408a and 408b hold the two plate halves 502a and 502b in a coplanar arrangement, with the fastener apertures in the plates aligned with the respective sets of fastener guides 410a/410b. The compression attachment mechanism 406 allows for the implant positioning device 400 to be coupled to and uncoupled from the plates 502a and 502b quickly and easily, simply by compressing the spring loaded mechanism.

The implant positioning device 400 may also be adapted to accommodate different plate geometries. Additionally, the implant positioning device 400 may also have clamping or connectable features in a plane opposite the attachment feet 408a and 408b, such as another set of feet oriented about 90 degrees from the attachment feet 408a and 408b. These feet may also thread into holes or attach in a number of different ways to plates and other devices.

The compression locking mechanism 474, as illustrated, is a threaded turn knob disposed on a top of the implant positioning device 400. The compression locking mechanism 474 may be tightened, for example, by turning the compression locking mechanism 474, to place a compression force against an inner rail of the compression attachment mechanism 406 to lock the compression attachment mechanism 406 in a desired position. While the compression locking mechanism 474 is illustrated as a threaded turn knob, the compression locking mechanism 474 may be any number of locking mechanisms, for example, one or more levers, cams, etc. that are configured to lock the compression attachment mechanism 406 in a desired position. These mechanisms may also be designed such that a user can only place fasteners 114 into the guide barrels of the first and second sets of fastener guides 410a and 410b when the implant positioning device 400 is in a locked position. In this aspect, the locking mechanism may cover the guide barrels of the first and second sets of fastener guides 410a and 410b in an unlocked position.

The handle 404 may be removably coupled to the implant positioning device 400 and is used to retain the implant positioning device 400 in a particular position for ease of assembly of elements (such as the plates 502 and 502b) that may be connected to it. The handle 404 may also include a grip 476 with an ergonomic design for comfort and control of the implant positioning device 400.

The implant positioning devices 100, 300 and/or 400 may be adapted or modified to accommodate different plate geometries. Additionally, one or more features of the implant positioning devices 100, 300 and/or 400 may be incorporated into the other implant positioning devices 100, 300 and/or 400. For example, the implant positioning device 300 may include the locking mechanism and the handle described in connection with the implant positioning device 400. Similarly, the fastener housings of the first and second sets of fastener guides 110a and 110b/310a and 310b may be adapted to swivel to allow for varying degrees of angular positions for guiding the fasteners 114. The fastener housings of the first and second sets of fastener guides 110a and 110b/310a and 310b may individually be slidable along a shaft or bar to allow the position of each respective fastener housing of the first and second sets of fastener guides 110a and 110b/310a and 310b to be adjusted. Further, a length and diameter of the fastener housings of the first and second sets of fastener guides 110a and 110b/310a and 310b may also be varied to accommodate different lengths of fasteners and fasteners of different diameters.

The locking mechanism incorporated into the implant positioning devices 400 may be the turn knob described above, or may be another type of locking mechanism. For example, the locking mechanism may be a rack and pinion, ratchet, lever, a switch, or other type of locking mechanism known in the art.

The implant positioning devices 100, 300 and/or 400 may be used in conjunction with any device that utilizes screws, drills, pins, and/or other types of fasteners or drilling device that involve directional alignment, positioning, etc. prior to final fixation. For example, the implant positioning devices 100, 300 and/or 400 may be used to guide a drill bit and then also be used to place a screw or other fastener.

The implant positioning devices 100, 300 and/or 400 may be used in conjunction with any type of bone plate or other type of plate. For example, the implant positioning devices 100, 300 and/or 400 may be for used for fixation of boney elements to prevent motion in a particular direction as well as providing dynamic stabilization.

The sets of fastener guides, for example, the first and second sets of fastener guides 110a and 110b/310a and 310b may have a base profile proximal to the plate(s) 200 that is extended as compared to the implant positioning device 400, to conform to a shape of the plate(s) 500. This serves as a loading tool for the plate(s) 200 and/or 500. For example, the base profile of the first and second sets of fastener guides may be keyed so left and right are not commingled. The base profile of the first and second sets of fastener guides may also provide stabilization when the fasteners are driven into the bone or other part of a patient's body to prevent torqueing of the plate/device. Thus, it preserves the orientation of each plate respectively to the other.

The implant positioning devices 100, 300 and/or 400 may be used to fix plates or other implant devices, as well as remove such devices. For example, the implant positioning devices 100, 300 and/or 400 may be used for screw or fastener removal. In this aspect, the fastener(s) may be pulled into the guide barrels of the first and second sets of fastener guides and held by the fastener captive elements to prevent the fasteners from falling into the patient.

The sets of fastener guide may also be wholly or partially transparent to allow the user to view the progress of the fastener being inserted/driven. The sets of fastener guides may also each include one or more fastener housings to accommodate or be agnostic to varying plate(s) and other devices with a single or more than one fastener aperture. The sets of fastener guides may also be adjustable, to accommodate shorter, wider, longer, etc. plate(s) and other devices of the type.

Although the devices, systems, and methods have been described and illustrated in connection with certain embodiments, many variations and modifications should be evident to those skilled in the art and may be made without departing from the spirit and scope of the disclosure. The disclosure is thus not to be limited to the precise details of methodology or construction set forth above as such variations and modification are intended to be included within the scope of the disclosure.

What is claimed is:

1. A device for positioning an orthopaedic fixation device, comprising:
   a compression attachment mechanism comprising an attachment feature and at least one spring configured to removably couple the attachment feature to a plate;
   a fastener guide coupled to the compression attachment mechanism and configured to receive a fastener; and
   a spring member disposed entirely in the fastener guide and configured to hold the fastener in the fastener guide.

2. The device of claim 1, wherein the attachment feature of the compression attachment mechanism includes attachment feet adapted to removably couple the plate to the compression attachment mechanism in alignment with the fastener guide.

3. The device of claim 1, wherein the spring member includes a collar and one or more prongs extending downwardly from the collar.

4. The device of claim 3, wherein the spring member includes three prongs extending downwardly from the collar.

5. The device of claim 1, wherein the fastener guide includes a first fastener guide and a second fastener guide disposed on opposing sides of the compression attachment mechanism.

6. The device of claim 5, wherein each of the first fastener guide and the second fastener guide include a plurality of fastener housings configured to receive individual fasteners.

7. A combined guide and holder for fasteners used in orthopaedic fixation, wherein a plate is to be affixed to a bone, comprising:
- a base adapted to align with the plate in a manner to orient fasteners with the plate for fixation;
- a plurality of fastener holders on the base, each fastener holder adapted to releasably hold a fastener in a manner where the fastener is exposed at a proximal end for access by a fastener driver and aligned at a distal end with an aperture in the plate through which the fastener is to be driven; and
- a compression attachment mechanism comprising an attachment feature and at least one spring configured to removably couple the attachment feature to the plate, wherein the at least one spring bears against the base and compression of the at least one spring in a compression direction causes a corresponding movement of the attachment feature parallel to the compression direction.

8. The device of claim 7, wherein the plurality of fastener holders are tubular.

9. The device of claim 8, further comprising a biasing element extending inboard from a tubular sidewall holding an individual fastener in an individual fastener holder.

10. The device of claim 9, wherein multiple biasing elements are spaced about the tubular sidewall to center the individual fastener.

11. The device of claim 7, wherein the base includes a recess sized and shaped to receive the plate.

12. A device for positioning an orthopaedic fixation device, comprising:
- a base, including:
  - a mounting structure;
  - a first fastener guide coupled to the mounting structure; and
  - a second fastener guide coupled to the mounting structure, wherein the mounting structure is between the first and second fastener guides; and
- a compression attachment mechanism coupled to the base and comprising an attachment feature and at least one spring configured to removably couple the attachment feature to a plate such that the compression attachment mechanism is configured to releasably hold the plate and align the plate with at least one of the first and second fastener guides, wherein the at least one spring bears against the base and compression of the at least one spring in a compression direction causes a corresponding movement of the attachment feature parallel to the compression direction.

13. The device of claim 12, wherein each of the first and second fastener guides include a fastener housing configured to receive a fastener.

14. The device of claim 13, further comprising a spring member disposed in the fastener housing and configured to hold the fastener in the fastener guide.

15. The device of claim 12, wherein each of the first and second fastener guides include a bottom recess sized and shaped to receive the plate.

16. The device of claim 15, wherein the compression attachment mechanism releasably holds the plate in the recess.

17. The device of claim 12, wherein the base further includes a spike extending from a bottom of the base to assist in placing and holding the device.

18. A device for positioning an orthopaedic fixation device, comprising:
- a compression attachment mechanism comprising an attachment feature and at least one spring configured to removably couple the attachment feature to a plate;
- a fastener guide coupled to the compression attachment mechanism and configured to receive a fastener; and
- a spring member disposed in the fastener guide and configured to hold the fastener in the fastener guide, wherein the compression attachment mechanism includes:
  - first and second supports;
  - a first rail extending through the first support, through a first aperture in a mounting structure of the fastener guide, and coupled to the second support;
  - the at least one spring which comprises a first spring is disposed on the first rail between the first support and the mounting structure;
  - a first stop disposed on the first rail between the first spring and the first support; and
  - a first gripping portion coupled to the first rail proximal to the first support.

19. The device of claim 18, wherein the first spring is configured to compress between the first stop and the mounting structure upon application of a force in a direction towards the second support.

* * * * *